US011419890B2

(12) United States Patent
Dake et al.

(10) Patent No.: US 11,419,890 B2
(45) Date of Patent: Aug. 23, 2022

(54) COMPOSITIONS PREPARED FROM POULTRY AND METHODS OF THEIR USE

(71) Applicant: INTERNATIONAL DEHYDRATED FOODS, INC., Springfield, MO (US)

(72) Inventors: Roger L. Dake, Springfield, MO (US); Stephanie Lynch, Springfield, MO (US); Paul L. Durham, Nixa, MO (US); Ryan J. Cady, Springfield, MO (US); Jordan L. Hawkins, Springfield, MO (US)

(73) Assignee: INTERNATIONAL DEHYDRATED FOODS, INC., Springfield, MO (US)

( * ) Notice: Subject to any disclaimer, the term of this patent is extended or adjusted under 35 U.S.C. 154(b) by 0 days.

(21) Appl. No.: 16/676,333

(22) Filed: Nov. 6, 2019

(65) Prior Publication Data
US 2020/0061101 A1 Feb. 27, 2020

Related U.S. Application Data

(63) Continuation of application No. 14/325,694, filed on Jul. 8, 2014, now Pat. No. 10,555,967.
(Continued)

(51) Int. Cl.
A61K 31/737 (2006.01)
A61K 31/401 (2006.01)
(Continued)

(52) U.S. Cl.
CPC .......... A61K 31/737 (2013.01); A61K 31/401 (2013.01); A61K 31/4172 (2013.01); A61K 35/57 (2013.01); A61K 45/06 (2013.01)

(58) Field of Classification Search
CPC .... A61K 45/06; A61K 31/401; A61K 31/737; A61K 35/57; A61K 31/4172;
(Continued)

(56) References Cited

U.S. PATENT DOCUMENTS 5,073,394 A 12/1991 Dake et al.
5,645,851 A 7/1997 Moore
(Continued)

FOREIGN PATENT DOCUMENTS

EP 1607006 A1 12/2005
EP 2205737 B1 2/2013
(Continued)

OTHER PUBLICATIONS

Krasnow et al., "Effects of Cooking Temperatures on the Physicochemical Properties and Consumer Acceptance of Chicken Stock" Journal of Food Science vol. 71 No. 1 pp. 219-S23 (Year: 2012).*
(Continued)

Primary Examiner — Eric Olson
(74) Attorney, Agent, or Firm — Lathrop GPM LLP

(57) ABSTRACT

Broth compositions prepared from poultry are disclosed. Selected poultry raw materials are processed to obtain a broth having high protein content. Certain specific amino acids are present in relatively higher concentration as compared to home-made broth and other commercial products. The disclosed broth compositions are effective in preventing and/or treating joint diseases and may also provide other nutritional and health benefits.

13 Claims, 3 Drawing Sheets
Specification includes a Sequence Listing.

Related U.S. Application Data

(60) Provisional application No. 61/843,662, filed on Jul. 8, 2013.

(51) Int. Cl.
*A61K 31/4172* (2006.01)
*A61K 45/06* (2006.01)
*A61K 35/57* (2015.01)

(58) Field of Classification Search
CPC ....... A61K 2300/00; A61K 38/39; A61P 3/10; A61P 29/00; A61P 25/28
See application file for complete search history.

(56) References Cited

U.S. PATENT DOCUMENTS

| | | | |
|---|---|---|---|
| 6,025,327 A | 2/2000 | Alkayali | |
| 6,323,319 B1 * | 11/2001 | Alkayali | C07K 14/78 435/212 |
| 6,780,841 B2 * | 8/2004 | Ishaq | C12P 19/26 514/17.2 |
| 7,671,041 B2 | 3/2010 | Vouland et al. | |
| 8,288,356 B2 | 10/2012 | Obad et al. | |
| 8,481,072 B2 | 7/2013 | Minatelli et al. | |
| 8,507,757 B2 | 8/2013 | Minatelli et al. | |
| 8,524,980 B2 | 9/2013 | Minatelli et al. | |
| 8,557,275 B2 | 10/2013 | Minatelli et al. | |
| 8,679,551 B2 | 3/2014 | Ruff | |
| 8,927,032 B2 | 1/2015 | Ruff | |
| 8,945,608 B2 | 2/2015 | Minatelli et al. | |
| 8,962,924 B2 | 2/2015 | Minatelli et al. | |
| 8,999,373 B2 | 4/2015 | Minatelli et al. | |
| 9,028,814 B2 | 5/2015 | Minatelli et al. | |
| 9,034,366 B2 | 5/2015 | Minatelli et al. | |
| 9,050,364 B2 | 6/2015 | Minatelli et al. | |
| 9,216,164 B2 | 12/2015 | Minatelli et al. | |
| 9,238,043 B2 | 1/2016 | Minatelli et al. | |
| 10,555,967 B2 * | 2/2020 | Dake | A61P 3/10 |
| 2002/0086070 A1 | 7/2002 | Kuhrts | |
| 2005/0148073 A1 | 7/2005 | Hansen et al. | |
| 2012/0021063 A1 | 1/2012 | Matsumoto et al. | |
| 2014/0065205 A1 | 3/2014 | Anthony et al. | |
| 2016/0213752 A1 * | 7/2016 | Lynch | A23L 5/13 |

FOREIGN PATENT DOCUMENTS

| | | |
|---|---|---|
| JP | 4695846 B2 | 6/2011 |
| MX | 2011012090 A | 5/2013 |

OTHER PUBLICATIONS

Durham et al., "Dietary Inclusion of Chicken Broth AAC1 Inhibits Mechanical Hyperalgesia and Increased PKA Expression: Evidence Blocking Peripheral and Central Sensitization in the Trigeminal System" Headache vol. 56 Suppl 1, p. 61 abstract PS28 (Year: 2016).*

Kong et al., "Comparison of non-volatile umami components in chicken soup and chicken enzymatic hydrolysate" Food Research International vol. 102 pp. 559-566 http://dx.doi.org/10.1016/j.foodres.2017.09.038 (Year: 2017).*

Anonymous "Howto Make Bone Broth and Bone Broth's Health Benefits", Nov. 8, 2012 (Nov. 8, 2012), pp. 1-4, XP055563268. [Retrieved from the Internet: https://www.healthextremist.com/bone-broths-health-benetits-and-how-to-make-it/ [retrieved on Feb. 28, 2019]* p. 3-4 "How to Make Bone Broth" *].

European Patent Application No. 19200134.5, Extended Search and Opinion dated Mar. 26, 2020, 13 pages.

Extended European Search Report dated Feb. 9, 2017 for European Patent Application No. 14822469.4.

Connaughton (Nov. 2010), "From the Test Kitchen: Perfect Pressure Cooker Chicken Stock", Saveur, Nov. 8, 2010 (Nov. 8, 2010), pp. 1-3.

Du Souich et al. (Aug. 2009), "Immunomodulatory and anti-inflammatory effects of chondroitin sulphate", Journal of Cellular and Molecular Medicine, vol. 13, No. 8a, Aug. 1, 2009 (Aug. 1, 2009), pp. 1451-1463.

Sisson (Apr. 2010), "Mark's Daily Apple Cooking with Bones," Apr. 15, 2010 (Apr. 15, 2010 ), pp. 1-8.

Communication pursuant to Article 94(3) EPC dated Nov. 16, 2017 for European Patent Application No. 14822469.4 (8 pages).

Result of Formal Examination dated Mar. 22, 2016, for Colombian Patent Application No. 16-29211-2 (3 pages).

M.J. O'Neil et al., Merck Index, 14th Ed., Merck & Co. Whitehouse Station, NJ, 2006, only p. 368 supplied, see entry 2214.

Anon., Sigma Life Science, Products for Life Science Research, St. Louis, MO, 2008-2009, p. 475, see col. 1.

Vietnamese Patent Application No. 1-2016-00434, English translation of Office Action dated Jul. 31, 2020, 1 pages.

Canadian Patent Application No. 2,917,712, Office Action dated Jul. 17, 2020, 6 pages.

* cited by examiner

COMPOSITIONS PREPARED FROM POULTRY AND METHODS OF THEIR USE

RELATED APPLICATIONS

This application is a continuation of U.S. patent application Ser. No. 14/325,694, filed Jul. 8, 2014, which claims priority to U.S. Patent application 61/843,662 filed Jul. 8, 2013, the entire content of which each of these applications is hereby incorporated by reference into this application.

SEQUENCE LISTING

This application is accompanied by a sequence listing in a computer readable form that accurately reproduces the sequences described herein.

BACKGROUND

Chicken broth is a complex mixture containing extractives obtained from cooking of chicken parts or whole chickens. Different chicken broths may have different compositions which may explain the varying nutritional and health values of different broths. One major constituent of a chicken broth is soluble proteins, which are made up of albumins, along with many other proteins. Numerous other compounds are present in chicken broths. Examples of such compounds include, for example, minerals, organic compounds, nucleotides, metabolites, lipids, phospholipids, vitamins, among others.

Traditional home-style chicken broth is prepared by cooking one or more poultry parts in water and/or steam for extended time. Broths prepared from different raw materials may have different compositions. Even when the same raw materials are used, slight variations of the cooking processes may result in broths having different constituent profiles.

SUMMARY

The present disclosure advances the art by providing broth compositions prepared from poultry and methods of preparing and using the same. In one embodiment, the disclosed composition may be prepared from poultry, such as, for example, chicken, turkey, or other birds. In another embodiment, the disclosed composition may be prepared using parts from other animal sources. In another embodiment, the disclosed composition may be in the form of broth, stock, extract, or powder.

In one aspect, the composition prepared according to the disclosed methods may have higher concentration of certain beneficial compounds. In another aspect, certain beneficial compounds may be enriched in the disclosed compositions to a greater extent as compared to other broth products currently available on the market. In another aspect, one or more ingredients may be supplemented in the broth to achieve certain health benefits that are not generally associated with chicken broth. Examples of such supplements may include but are not limited to ginger, coffee extract, *ginseng*, green tea, other botanicals such as willow bark or boswellia, curcumin/turmeric, omega-3 fatty acids, fish oil, krill oil, algal oil, Pycnogenol French maritime pine bark extract, grape seed extract, flax seed extract, ribonuclease, angiogenin, lactoferrin, ribonuclease-enriched lactoferrin, S-adenosyl methionine, collagen, collagen proteins or collagen peptides, gelatin, avocado/soybean unsaponifiables (ASU), extract of hops cones, egg shell membrane, polypeptides derived from milk, such as casein or whey, MSM (Methylsulfonylmethane), *Yucca*, Devils claw, Bromelain, glutamic acid, cocoa, stinging nettle, Vitamin E, Vitamin D3, walnut extract, etc. In one aspect, the disclosed broth may contain significant amount of collagen, collagen proteins and/or collagen peptides. In another aspect, significant amount of the collagen, collagen proteins and/or collagen peptides may be present naturally in the disclosed broth. In another aspect, significant amount of the collagen, collagen proteins and/or collagen peptides may be added into the disclosed broth as a supplement.

In home-style cooking, chicken or turkey broths may be made by cooking for extended period of time in an open vessel or under high temperature in a pressurized vessel. By contrast, this disclosure provides broth products having unique composition and methods of preparing the same. Also disclosed here are methods of selecting and preparing raw materials, cooking raw materials, and separating and purifying the resultant broths.

In one embodiment, raw materials from poultry or other animal sources may be comminuted to a great extent to maximize extraction of various beneficial compounds. In one aspect, the raw materials may be reduced to a size of less than about 2 cm, 1 cm, 5 mm, 4 mm, 3 mm, 2 mm, or less than 2 mm. Mechanical processing of the poultry parts to small sized particles prior to cooking may help maximizing extraction of certain compounds. In another embodiment, because the poultry parts have been mechanically processed to very small-sized particles prior to cooking, more gentle cooking condition (e.g., at a temperature of 60-100° C.) and shorter cooking time (from about 8 minutes to 300 minutes) may be used to obtain the broth from the processed poultry parts. Such gentler and shorter cooking may help prevent inactivation of certain compounds that would be otherwise inactivated if conventional processing and cooking methods are used. Preservation of such compounds may explain the superior health benefits observed when the disclosed broths are tested against other broth products that are not prepared according to the instantly disclosed methods.

In another embodiment, poultry parts with bones and cartilage may be mechanically separated and comminuted to fine pieces of less than 5 mm (millimeter), 4 mm, 3 mm, 2 mm, or 1 mm in size. In one aspect, no steps are taken to remove the residual meat from the bones. These small pieces may be cooked at about 70° C., 100° C., 110° C., 120° C., or as high as 150° C., for at least 8 minutes, 15 minutes, 30 minutes, 1 hour, 2 hours, 3 hours, or 6 hours or longer to maximize the extraction of certain broth fraction and/or compounds.

In another embodiment, the broth prepared according to the disclosed methods show different protein profiles from those obtained from other commercial broth products when analyzed by SDS-PAGE. In one aspect, at least 10%, 20%, 30%, 40%, 50%, 70%, or 90% of the total proteins in the disclosed compositions have a molecular weight of between 10 kD (kilo-Dalton) and 70 kD. In another aspect, at least 95% of the proteins in the disclosed compositions have a molecular weight of less than 100 kD. In another aspect, the methods may be used to further reduce molecular weight of the proteins in the broth to less than 10 kD, 5 kD, or even lower than 3 KD to enhance assimilation by a subject. By way of example, one or more enzymes that digest proteins may be used to reduce the molecular weight of the proteins in the broth.

In another embodiment, the disclosed composition may contain the amino acids proline and histidine, wherein the ratio between proline and histidine is at least 4:1 by weight. In one aspect, the proline is present in the composition by at least 8% (w/w), 10% or greater on solid basis. In another aspect, the ratio between the proline and the histidine is at least 6:1 by weight.

In another embodiment, the disclosed composition may contain the amino acids glycine and histidine, wherein the ratio between the glycine and histidine is at least 6:1 by weight. In one aspect, the glycine is present in the composition by at least 12%, 14% or greater (w/w) on solid basis. In another aspect, the ratio between the glycine and the histidine is at least 10:1 by weight.

In another embodiment, the disclosed composition may contain the amino acids hydroxyproline and histidine, wherein the ratio between the hydroxyproline and histidine is at least 4:1 by weight. In one aspect, the hydroxyproline is present in the composition by at least 7%, 8% or greater (w/w) on solid basis. In another aspect, the ratio between the hydroxyproline and the histidine is at least 6:1 by weight.

In another embodiment, the disclosed composition may contain proline, glycine, hydroxyproline and histidine. In one aspect, the ratio between the glycine and the histidine is at least 6:1 by weight. In another aspect, the glycine is present in the composition by at least 12% (w/w) on solid basis. In another aspect, the ratio between the proline and the histidine is at least 4:1 by weight. In another aspect, the ratio between the hydroxyproline and the histidine is at least 6:1 by weight.

In another embodiment, the disclosed composition may contain proline and other amino acids, and the amount of the proline is at least 10% by weight of the total amino acids in the composition. In another embodiment, the disclosed composition may contain glycine and other amino acids, and the amount of the glycine is at least 20% by weight of the total amino acids in the composition. In another embodiment, the disclosed composition may contain hydroxyproline and other amino acids, and the amount of the hydroxyproline is at least 8% by weight of the total amino acids in the composition.

In another embodiment, the disclosed composition may contain one or more branched chain amino acids (BCAA) (e.g., valine, leucine and isoleucine), and the BCAAs in the composition are present at a higher level than the level of BCAAs in other broth products. In one aspect, the amount of total BCAAs, including valine, leucine and isoleucine, is at least 5%, 6%, or 7% by weight of total amino acids in the composition.

In another embodiment, the broth products prepared according to this disclosure may have a moisture protein ratio (MPR) of between 999:1 and 1:999, or between 200:1 and 10:1. By way of example, a MPR of 200:1 means the product contains 200 parts water and 1 part meat (protein). In another embodiment, the broth products prepared according to this disclosure may have a moisture protein ratio (MPR) of between 150:1 and 40:1, or between 135:1 and 67:1.

Chondroitin sulfate (CS) is rich in cartilage and has been reported to be beneficial for joint health. The selection of raw materials and the process by which the broth is prepared may contribute to the relatively higher levels of chondroitin sulfate in the disclosed composition. In one embodiment of the present disclosure, the broth composition may contain at least 6%, 7%, 8%, or 10% of chondroitin sulfate by weight of total dry solids in the composition, as measured by using enzymatic digestion and LC-UV detection assay. See e.g., Ji et al., Journal of AOAC International, Vol. 90, No. 3, 659-69 (2007), which is hereby incorporated by reference into this disclosure.

In one aspect, the composition may be in a liquid form ready to be consumed or it may be in a concentrated liquid form such as a stock. In another aspect, the composition may be in a solid form, such as a powder or a paste.

In one embodiment, the composition may contain one or more polyphenols, wherein the concentration of the polyphenols is at least 4,000 μg/ml GAE (Gallic Acid Equivalent) based on Folin-Ciocalteu assay.

The broths disclosed herein may be characterized by the unique composition as described above. The broths may also be characterized by the methods through which they are prepared. Moreover, the disclosed broths are also unique in the health benefits they may provide to a subject. Subjects may be divided into two groups, one group ingests (or consumes) an effective amount of the disclosed broth product each day, while the other group ingests water, or other broth products. The various indicators may then be measured and compared between the two groups.

In one embodiment, the composition disclosed herein may reduce pain significantly in a subject when it is administered to the subject as compared to a subject not administered the composition. For purpose of this disclosure, "significantly" means the observed difference between the treatment group and the control group is statistically significant.

Protein Kinase A (PKA) is a family of cyclic AMP (cAMP) dependent enzymes implicated in inflammation. In another embodiment, the composition may significantly reduce stress-induced expression of protein kinase A (PKA) in a subject administered said composition as compared to a control subject not administered said composition. In one aspect, the composition reduces expression of protein kinase A (PKA) by 20%, 30%, by 50% or greater in a subject administered said composition as compared to a control subject not administered said composition.

In another embodiment, the disclosed compositions may substantially inhibit activity of cyclooxygenase (COX)-2 as measured by using a COX Inhibitor Screening Assay. In one aspect, the inhibition of COX-2 is greater than 20%, 30%, or 40%, as compared with subject with no administration of the composition. In another aspect, the disclosed composition causes no significant inhibition of COX1 as measured by using a COX Inhibitor Screening Assay. In another aspect, the ratio of inhibition between COX2 and COX1, i.e., COX2/COX1 exerted by the instant composition is between 2 and 30, between 5 and 20, or between 10 and 20.

In one embodiment, it is provided here methods for preventing or treating various diseases by administering to a subject an effective amount of a composition prepared according to the instant disclosure. In another embodiment, the disclosed methods may further include a step of identifying subjects who are in need of treatments. In one aspect, the subject may be susceptible to one or more of the diseases. In another aspect, the subject may already have one or more of the diseases. Examples of the diseases may include but are not limited to joint disease, inflammation, autoimmune disease, diabetes, metabolic disorder, cognitive disorder and combination thereof.

In one aspect, the effective amount may be an amount of the composition that significantly reduces stress-induced expression of protein kinase A (PKA) as compared to a control subject who has not been administered the composition. In another aspect, the composition may reduce expression of the protein kinase A (PKA) by at least 50% in a subject administered the composition as compared to a control subject who has not been administered an effective amount of the composition.

In another aspect, the effective amount may be an amount of the composition that inhibits COX-2 activity by at least 20% in the subject while not significantly inhibiting COX1 activity. In another aspect, the ratio of inhibition between COX2 and COX1 exerted by the composition is between 2 and 30.

In another aspect, the effective amount is an amount of the composition that significantly reduces nociception (pain) as compared to a control subject who has not been administered an effective amount of the composition.

MicroRNAs (miRNAs) are small RNA molecules that can regulate gene expression. miRNAs have been implicated in the development and progression of many inflammatory diseases. In one embodiment, when administered to a subject, the composition may decrease expression of a miRNA in a subject administered an effective amount of said composition as compared to a control subject not administered said composition. Examples of such miRNA may include but are not limited to SEQ ID Nos. 1-16, 18-26, and 28-43.

In one embodiment, the disclosed methods help prevent and/or treat inflammation and/or autoimmune disease. In one aspect, the composition decreases expression of at least one miRNA in the subject receiving an effective amount of the composition as compared to expression of the same miRNA in a control subject not receiving the effective amount of the composition. Examples of the miRNA associated with these methods include, for example, one or more of SEQ ID Nos. 1-16, and 18-26.

In another embodiment, the disclosed methods help prevent and/or treat diabetes and/or a metabolic disorder. In one aspect, the composition decreases expression of at least one miRNA in the subject receiving an effective amount of the composition as compared to expression of the same miRNA in a control subject not receiving the effective amount of the composition. Examples of the miRNA associated with these methods include, for example, one or more of SEQ ID Nos. 28-33.

In another embodiment, the disclosed methods help prevent and/or treat a cognitive disorder. In one aspect, the composition decreases expression of at least one miRNA in the subject receiving an effective amount of the composition as compared to expression of the same miRNA in a control subject not receiving the effective amount of the composition. Examples of the miRNA associated with these methods include but are not limited to one or more of SEQ ID Nos. 34-43. Examples of cognitive disorders include, for example, schizophrenia, autism, Alzheimer's disease, among others.

In another embodiment, when administered to a subject, the composition may increase expression of a miRNA in a subject administered an effective amount of said composition as compared to a control subject not administered said composition. Examples of such miRNA may include but are not limited to SEQ ID No. 17 and SEQ ID No. 27.

DETAILED DESCRIPTION

Figure 1:
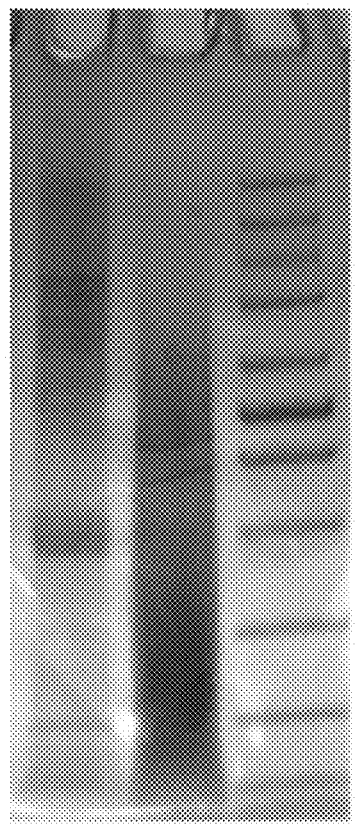
FIG. 1 shows the protein profile by staining of proteins separated by SDS-PAGE.

Chicken soup and chicken broth have been available for human consumption for centuries. Many studies have been performed that show various health benefits of chicken soup or broth. According to conventional home-style method, chicken soup or broth is prepared by boiling whole chicken or large chicken parts in a pot of water for an extended period of time. The soup or broth prepared according to this method may not have maximized the health promoting effects of the soup or broth because some of the compounds may have been lost during cooking or during processing, while other compounds may not have been extracted from the chicken parts.

The present disclosure provides an improved method by processing chicken parts prior to cooking and by controlling the processing temperature and cooking time to maximize the extraction of beneficial compounds while, concomitantly, minimizing loss of activity due to harsh processing conditions.

Specially selected raw materials from poultry are processed according to the disclosed methods to obtain a broth having high protein content. Certain amino acids are present in relatively higher concentration as compared to a home-made broth or other commercial products. As shown in various animal studies described herein, the disclosed broth compositions may prove effective in preventing and/or treating joint diseases and the underlying pathology. The compositions may also provide other nutritional and health benefits such as decreasing inflammation.

The terms "broth" and "soup" refer to a liquid composition containing at least one solute and may also be used to refer to a ready to serve form, a concentrate, a stock in either liquid or solid form.

The poultry broth of the disclosure may contain a significant amount of different amino acids. Such amino acids may be present in the form of a protein or as free amino acids in the broth. Total amino acids include both amino acids present in the form of proteins and those present as free amino acids. For purpose of this disclosure, the ratio of different amino acids in a broth composition refers to the ratio between total amino acids.

The term "dry solid" or "solid" as used herein refers to the components of a liquid composition that remain after all free liquid is removed from the liquid composition. In the case of an aqueous broth, the free liquid is water.

The term "administer" means delivering of a material to an individual, such as by oral ingestion.

The term "subject" is used to refer to a mammal, including human being.

The term "substantially" means by at least 10-20%.

EXAMPLES

The following examples are provided for purposes of illustration of the embodiments only and are not intended to be limiting. The raw materials, reagents, chemicals, and other materials are presented as exemplary components or reagents, and various modifications may be made in view of the foregoing discussion within the scope of this disclosure. Unless otherwise specified in this disclosure, components, reagents, protocol, and other methods used in the system and the assays, as described in the Examples, are for the purpose of illustration only.

Example 1 Preparation of Broth from Turkey Parts

In this example, turkey parts were used to prepare a broth and the overall quality and potential health benefits of the broth were determined. Briefly, raw turkey was mechanically separated and the parts were finely comminuted to less than 2 mm in size to maximize extraction. The small-sized parts from the turkey were gently cooked to 195° F. in steam for about 15 minutes or less. The broth was then separated from the insoluble fraction by decanting. Freed fat in the broth was also removed from the broth by a centrifugal separator. The broth was concentrated in a commercial evaporator, chilled, and packaged for sale.

Example 2 Preparation of Broth from Chicken Parts

In this study, chopped chicken parts containing chicken bones and cartilage were cooked in water at a temperature greater than 250° F. for more than 6 hours to maximize the extraction of certain broth fraction and/or compounds. The broth obtained from this process was designated "AAC1" for internal reference. More particularly, USDA inspected chopped raw chicken bones remaining after major muscles were removed were cooked in water in a large commercial stainless steel cooking tank. After cooking, the liquid broth portion was separated from the chicken solids by decanting. The broth was concentrated in a commercial evaporator then spray dried and packed in labeled containers.

Example 3 Comparing the Protein and Amino Acid Profiles of Different Broths

Proteins are large molecules composed of one or more chains of amino acids that perform a wide array of functions in biological systems including, for example, functioning as enzymes, facilitating cell communication, and providing structural support to cells. Humans, as well as other animals, obtain essential amino acids from protein consumed as part of their diet since they lack enzymes needed to synthesize them. Ingestion of proteins leads to their break down into amino acids through the digestive process. The amino acids can then be used in protein biosynthesis in muscle production and maintenance, glucose production, serve as a dietary nitrogen source, and serve as a fuel source if necessary. The objective of this study was to determine the concentration and size range of proteins in chicken broth AAC1 as compared to a home-made product.

One sample prepared according to this disclosure (AAC1) and another sample prepared according to home-style cooking methods (Homemade) were compared. The percent solid (w/v) for AAC1 was 8% solid, while the percentage (w/v) for Homemade was 1.7% solid.

Prior to determining the amount of protein by the Bradford method, each sample was diluted in distilled water to a final 1% w/v solution. A standard curve was prepared using bovine serum albumin (0-3.5 µg/µL). All samples were analyzed in triplicate. The amount of total protein was determined using a plate reader at a wavelength of 595 nm. Results are shown in Table 1.

TABLE 1

Amount of total protein in broth samples

| Sample | Values | Results | Mean Results | Concentration | SD | CV |
|---|---|---|---|---|---|---|
| AAC1 | 0.446 | 1.558 | 1.691 | 1.691 | 0.132 | 7.8 |
|  | 0.461 | 1.693 |  |  |  |  |
|  | 0.474 | 1.821 |  |  |  |  |
| Homemade | 0.544 | 2.496 | 2.52 | 2.52 | 0.034 | 1.3 |
|  | 0.549 | 2.544 |  |  |  |  |

To correct for differences in the percent solids in AAC1 (8%) and Homemade (1.7%) samples, the protein values based on a 1% solution for AAC1 and Homemade were multiplied by their respective starting % solids. The final adjusted amount of total protein for AAC1 and Homemade are shown in Table 2.

TABLE 2

Adjusted total protein concentration in AAC1 and homemade broth

| Sample | Adjusted Final Concentration | % of AAC1 |
|---|---|---|
| AAC1 | 13.6 µg/ul | — |
| Homemade | 4.3 µg/ul | 31.6% |

To determine the protein profile of each sample, equal volumes of the AAC1 and Homemade samples (15.6 µl) were each mixed with Laemmli's sample buffer and a reducing agent, heated at 95° C. for 5 minutes, and separated on a 4-12% Bis Tris gel. The relative size range of the proteins was determined by comparison to a commercially available protein standard (ranging from 4.5 kDa to 300 kDa). A constant voltage of 150V was applied to the gel for 30 minutes, allowing for separation of proteins in each sample. The proteins were visualized in the gel using SimplyBlue™ SafeStain.

The results are shown in FIG. 1. Lane 1 shows the protein profile for homemade broth, lane 2 for the AAC1 broth, and lane 3 is molecular weight standard. Based on the protein profiles, AAC1 is composed of approximately 3 times more protein than a homemade product. Proteins in the homemade product displayed a wider range of molecular weight distribution, containing both large (up to about 300-500 kD) and small proteins (about 5-15 kD). By contrast, the majority (i.e., greater than 50%) of proteins in AAC1 has molecular weight of between 70 kDa and 15 kDa.

Individual amino acid content was also analyzed. Table 3 below shows the individual amino acid content of the broth compositions prepared according to the disclosed methods as compared to those prepared using home-style methods as well as other commercial products.

TABLE 3

Amino acid composition of different broths

Table Two: Content values above calculated to 100% solids basis:

| | 3823 W/W % | Commercial product % | Home-made-1 | Home-made-2 | AAC1-1 | AAC1-2 | AAC1-3 |
|---|---|---|---|---|---|---|---|
| TAURINE | 2.50 | | | | | | |
| ASPARTIC ACID | 3.63 | 2.44 | 3.63 | 3.47 | 7.04 | 5.34 | 5.38 |
| THREONINE | 1.44 | 0.76 | 1.52 | 1.42 | 1.75 | 2.13 | 1.79 |
| SERINE | 1.56 | 1.34 | 1.96 | 1.89 | 2.08 | 1.88 | 2.40 |
| GLUTAMIC ACID | 10.25 | 6.98 | 9.44 | 9.26 | 10.52 | 9.50 | 10.14 |
| PROLINE | 3.53 | 3.05 | 5.93 | 5.57 | 9.59 | 10.66 | 11.07 |
| HYDROXYPROLINE | 2.19 | 2.99 | 5.31 | 4.92 | na | 7.00 | 9.39 |
| GLYCINE | 5.97 | 7.38 | 8.79 | 9.47 | 18.02 | 15.41 | 17.68 |
| Lanthionine | 0.06 | 0.00 | 0.00 | 0.00 | 0.00 | 0.00 | 0.00 |
| ALANINE | 3.91 | 3.37 | 4.60 | 4.58 | 8.06 | 7.53 | 7.53 |
| CYSTINE | 0.44 | 0.29 | 0.34 | 0.40 | 0.00 | 0.25 | 0.17 |
| VALINE | 1.44 | 0.73 | 1.43 | 1.42 | 2.44 | 2.19 | 2.21 |
| ISOLEUCINE | 1.13 | 0.47 | 1.18 | 1.02 | 1.54 | 1.59 | 1.59 |
| LEUCINE | 2.72 | 1.51 | 2.48 | 2.32 | 3.38 | 3.47 | 3.43 |
| METHIONINE | 0.81 | 0.52 | 0.93 | 0.77 | 1.01 | 1.06 | 1.10 |
| TYROSINE | 0.88 | 0.44 | 0.81 | 0.65 | 1.09 | 1.00 | 0.90 |
| PHENYLALANINE | 1.00 | 0.73 | 9.53 | 7.03 | 2.30 | 2.16 | 1.98 |
| HYDROXYLYSINE | 0.16 | 0.00 | 0.00 | 0.00 | 0.00 | 0.00 | 0.00 |
| HISTIDINE | 2.03 | 2.56 | 2.70 | 1.73 | 1.32 | 1.16 | 1.00 |
| ORNITHINE | 2.25 | 0.00 | 0.00 | 0.00 | 0.00 | 0.00 | 0.00 |
| LYSINE | 3.75 | 2.67 | 3.07 | 3.00 | 3.96 | 3.66 | 3.05 |
| ARGININE | 3.06 | 2.79 | 4.01 | 3.75 | 8.24 | 6.69 | 6.61 |
| TRYTOPHAN | 0.16 | 0.06 | 0.12 | 0.09 | | 0.22 | 0.15 |
| Total | 54.84 | 41.08 | 67.80 | 62.79 | 82.35 | 82.88 | 87.55 |

Example 4 Comparing Levels of Chondroitin Sulfate (CS) in Different Broths

Chondroitin sulfate (CS) is an important structural compound found in cartilage and is implicated in joint health. CS has been shown to reduce the levels of many inflammatory mediators such as iNOS, PGE2, COX-2 (Gwendolyn, Spine 2011), and NFkB (Valliéres, Osteoarthritis Cartilage, 2010). The goal of this study was to determine the amount of CS in various chicken broth samples. Chicken broths were analyzed for total CS using enzymatic digestion and LC-UV detection (Ji, Journal of AOAC International, 2007). Results were calculated as area on the curve compared to standard samples and the limit of quantification as 8 mg chondroitin sulfate/g dry material (Table 4). Among all chicken broths tested, AAC1 had the greatest amount of CS (8.797% w/w).

TABLE 4

Amounts of chondroitin sulfate (CS)

| Samples | Average (mg) | Dry mg/g | Dry % w/w |
|---|---|---|---|
| Powdered Chicken Broth AAC1 | 17.480 | 87.971 | 8.797 |
| Powdered Chicken Broth H814 | 15.443 | 67.553 | 6.755 |
| Frozen Concentrate TSN | 10.886 | 52.059 | 5.206 |
| Frozen Concentrate IDF Chicken 823 | 8.627 | 42.104 | 4.210 |
| Home Style Broth from Back Bones | 5.866 | 28.258 | 2.826 |
| Frozen Concentrate Turkey 824 | 5.243 | 26.227 | 2.623 |
| Powdered Chicken Broth HML 34511 | 4.979 | 24.335 | 2.434 |
| Powdered Chicken Broth A1004 | 3.817 | 18.305 | 1.830 |
| Powdered Chicken Broth P1301 | 3.075 | 15.054 | 1.505 |
| Home Style Broth from Chicken Parts | 2.185 | 10.99 | 1.09 |
| Home Style Broth from Chicken Necks | 1.937 | 9.361 | 0.936 |

Example 5 Comparison of Concentration of Polyphenols in Different Chicken Broths The concentration of polyphenols in different chicken broths was determined using a modified Folin-Ciocalteau method (Slinkard, American Journal of Enology and Viticulture, 1977). Polyphenols are a class of chemical compounds known to have anti-oxidant and anti-inflammatory properties. While both AAC1 and home-style broths contained polyphenols, AAC1 contained 4828.8 μg/mL GAE of polyphenols, which is approximately 7 times more GAE of polyphenols than a homemade broth (687.7 μg/mL GAE) made from the same kind of chicken parts.

Example 6 Effect of the Broth Composition on COX Family of Enzymes

The COX family of enzymes is responsible for the synthesis of prostanoids such as prostaglandins. COX-1 is constitutively active while COX-2 is inducible and hence is upregulated during inflammation and pain. Compounds that block COX-2 activation while not effecting COX-1 are of particular interest due to their ability to block inflammation while not causing unwanted side effects mediated by blocking COX-1 activity. The level and specificity of COX inhibition by the chicken broth prepared according to the disclosed methods was investigated.

Using an in vitro COX enzyme inhibitor assay (Abcam), chicken broth samples were assayed for their ability to block COX-1 and COX-2 activity according to the manufacturer's protocol. The results are shown in Table 5.

TABLE 5

Selective inhibition of COX-1 and COX-2

| Sample | Enzyme | % Inhibition | Ratio of COX2/COX1Inhibition |
|---|---|---|---|
| Powdered IDF AAC1 | COX-1 | −2.3 | 18.34 |
| | COX-2 | 42.4 | |
| Frozen IDF 823 | COX-1 | −51.5 | 0.43 |
| | COX-2 | 22.1 | |
| Home Style Broth from Back Bones | COX-1 | −17.9 | 1.57 |
| | COX-2 | 28.1 | |
| Home Style Broth from Necks | COX-1 | −32.5 | 0.78 |
| | COX-2 | 25.3 | |
| IDF Turkey 824 | COX-1 | −21.7 | 1.51 |
| | COX-2 | 32.7 | |
| Chicken Broth K | COX-1 | −25.5 | 1.21 |
| | COX-2 | 30.8 | |
| Commercial Broth TSN | COX-1 | −5.1 | 5.16 |
| | COX-2 | 26.3 | |
| Commercial Broth H814 | COX-1 | −39.9 | 0.28 |
| | COX-2 | 11.3 | |
| Commercial Broth A1004 | COX-1 | −9.2 | 4.01 |
| | COX-2 | 36.7 | |
| Commercial Broth HML | COX-1 | −27.0 | 1.01 |
| | COX-2 | 27.3 | |
| Commercial Broth PLNT | COX-1 | −19.9 | 2.36 |
| | COX-2 | 47.1 | |
| Home Style Broth from same raw parts | COX-1 | −5.2 | 0.67 |
| | COX-2 | 3.5 | |

Broth labeled "Home Style Broth from same raw parts" was a broth prepared using traditional home-style cooking method with the same raw materials as those used for preparing AAC1. As shown in Table 5 above, chicken broth AAC1 showed the greatest ratio of COX-2 inhibition to COX-1 inhibition (18.34) with greater than 40% inhibition of COX-2 enzyme activity as compared to other commercial products or "Home Style Broth from same raw parts."

Example 7 Effect of the Disclosed Broth on Joint Diseases by Regulating Protein Kinase A Temporomandibular Joint Disorder (TMD) is a disease affecting the temporomandibular or jaw joint (TMJ), the muscles of mastication, or both. TMD is believed to be caused by activation of neurons and glia cells located in the trigeminal system (Tjakkes et al., 2010). The prevalence of TMD symptoms have been reported in up to 93% in the general population with varying incidence rates (Zhao et al., 2011). Further development of TMD may also lead to the development of a chronically sensitized state of the disorder.

Protein kinase A (PKA) is a member of the family of cyclic AMP (cAMP) dependent enzymes that act as pro-inflammatory molecules in peripheral and central nervous systems. Increased levels of PKA expression by sensory nociceptive neurons has been reported during the chronic sensitized state. The objective of this study was to study the effects of commercially available broths, home-style broths, and the broths according to the instant disclosure. These various products may contain certain anti-inflammatory molecules that have some effects on TMD. These molecules may exert their effects through PKA in regulating the development and progress of TMD.

Three chicken broths (AAC1, TSN, and a homemade broth) were investigated in this study. Broth AAC1 (8% solids) was prepared at a concentration of 0.5% (w/v). First, 5 g of powdered broth was placed in a clean, autoclaved bottle. The bottle was then filled to the 1 L mark with filtered water and the mixture was stirred to allow the powder to dissolve in water. A homemade style broth (1.7%) was also tested as a control. To achieve a dosage that would allow for the comparison of AAC1 and the homemade-style broth, the homemade broth was diluted 16 fold with filtered water by placing 62.5 mL of stock broth and diluting the broth to 1 L. A commercially available broth, TSN, was also tested as another control. To ensure TSN was tested at a concentration similar to that of AAC1, the solution for TSN (33.3% solid) was made in a similar manner. The TSN broth was allowed to warm until a consistency of the stock broth was non-gelatinous. Broths were measured out into 16.7 g increments and placed into clean bottles as previously described. The bottle was then filled to the 1 L mark with filtered water. All solutions were then placed in a warm, sonication bath for 30 minutes to allow all components of the broths to be evenly solubilized. Broths were stored in the refrigerator until they were administered to the animals via water bottle administration for 2 weeks prior to TMD induction.

Adult Sprague-Dawley male rats (200 g-300 g) were used in this study. The rats were divided into three groups, with each group being fed with water, a commercial product (TSN), or AAC1 broth prepared according to this disclosure.

Mechanical stress was applied to each group and upper spinal cord tissues containing the spinal trigeminal nucleus (STN) samples were obtained and processed for immunostaining. Prior to immunostaining, slides were placed at room temperature and covered with 1×PBS for 5 minutes. PBS was removed, and liquid was replaced with a 5% normal donkey serum-0.1% triton solution for 20 minutes. Tissues were then washed with 5 mL 1×PBS. Working dilutions of rabbit anti-rat PKA (BD Biosciences, San Jose, Calif.; 1:500) were made using 5% normal donkey serum. Primary antibodies were allowed to incubate on tissues (100 μl/tissue) for 3 hours at room temperature. Samples were then washed with 5 mL 0.1% Tween 20-PBS and 2 mL 1×PBS. Working dilutions of donkey anti-rabbit IgG Alexa 488® was made by diluting stock antibodies 1:200 in 1×PBS. Secondary antibodies were allowed to incubate on sample slide (100 μl/tissue) for 1 hour at room temperature while protected from light. Slides were again washed with 5 mL 0.1% Tween 20-PBS and 2 mL 1×PBS, and mounted for fluorescent analysis using Vectashield fluorescent mounting media containing the fluorescent dye DAPI. Slides were cover slipped, sealed using clear nail polish, and stored at 4° C. until microscopic images were collected.

A Zeiss Z1 imager with apotome was used to acquire 10× Z-Stacked images of the V3 areas of the trigeminal ganglia and medullary horn of the STN. Zen 2011 software was used to evenly balance the background of each image prior to analysis. Gray scale jpeg images were opened in ImageJ software, where 10 non-overlapping regions of interests (RIOs) with an area of equal size were placed in areas representative of protein expression in each image, and the integrated pixel densities were measured. Background intensities were also acquired through similar procedure, and averaged. The average background intensity acquired from each image was then subtracted from each integrated density values from areas of interest. Subtracted integrated densities were averaged and fold changes were calculated as the average change±SEM from TMD control levels. Statistical differences were determined using the Mann-Whitney U test in SPSS software, and were considered to be different when $p \leq 0.05$.

Figure 2:
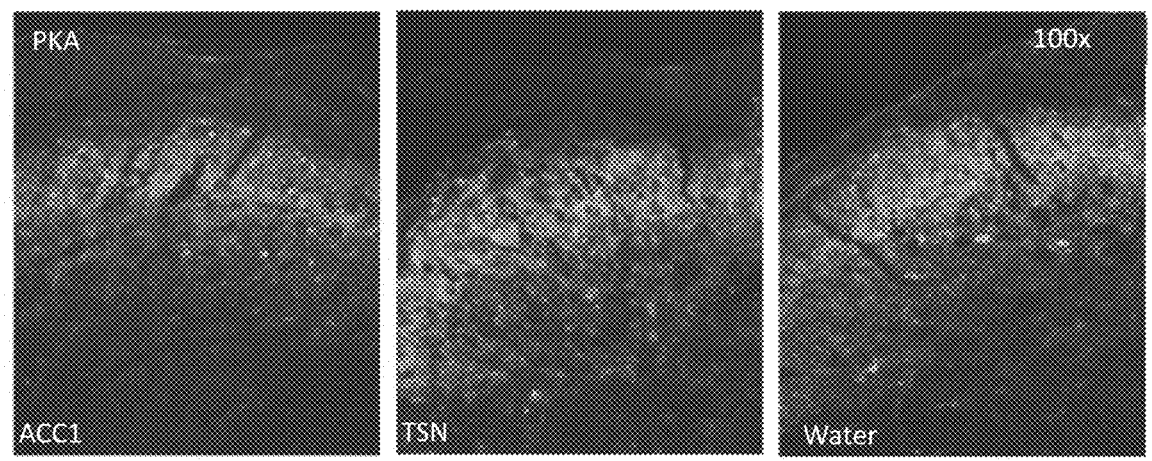
FIG. 2 shows that up-regulation of PKA is significantly repressed in animals fed with AAC1 broth as compared to animals fed with a commercially available product TSN.

The data in FIG. 2 provide evidence that elevated PKA levels caused by prolonged jaw opening are greatly repressed in AAC1 fed animals when compared to levels in animals consuming either water or a commercial product (TSN). In Table 6, the results of several experiments are summarized as the average fold change in the intensity of immunostaining when compared to water whose mean intensity was made equal to one.

TABLE 6

AAC1 repression of elevated PKA levels in response to jaw stress caused by prolonged jaw opening

| Broth | Average Fold Change | P Value (vs. TMD) | P Value (vs. TSN) |
|---|---|---|---|
| Water (TMD) | 1.00 ± 0.06 | 1.000 | 0.239 |
| AAC1 | 0.75 ± 0.02 | 0.001 | 0.000 |
| TSN | 0.94 ± 0.04 | 0.239 | 1.000 |

The AAC1 broth disclosed herein showed a greater ability to modulate the levels of PKA in the STN following joint stress when compared to a commercially available product. Based on the difference in composition of AAC1 and a homemade broth, we would predict that AAC1 would be significantly better at repressing stress-induced elevations in PKA levels in the STN.

Example 8 Nocifensive Responses of AAC1 as Compared to Other Broth Products

Temporomandibular Joint Disorder (TMD), is characterized by the continuation of pain behavior and sensation despite a decrease in nociceptive inputs (Herb et al., 2006). The increased sensitivity can be attributed to the development of a chronically sensitized state of the nerves that provide sensory innervation of the joint, muscles, ligaments, and tendons. TMD patients often report that their symptoms negatively affect other aspects of their life (Sessle, 2008). Some TMD patients develop protective behavior modifications that may limit or minimize their everyday activities. This protective behavior is termed "nocifensive" behavior. The objective of this study was to determine if AAC1 chicken broth could reduce TMJ stress-induced nocifensive behaviors in response to mechanical stimulation, and how its performance compares to homemade broth and commercially available products.

Three chicken broths (AAC1, TSN, and a home-style broth) were investigated in this study. Broth AAC1 (8% solids) was made at a 0.5% (w/v) while a homemade style broth (1.7%) was tested at a dose that would allow for an equal comparison of the ratio of percent solids between AAC1 and a homemade broth. Thus, the homemade broth was diluted 8 fold with filtered water by placing 62.5 mL of stock broth, and diluting the broth to 1 L. To test a competing commercially available broth at a similar concentration, a solution for TSN (33.3% solids) was made in a similar manner with the modification that the broth was allowed to warm until a consistency of the stock broth was non-gelatinous.

Broths were measured out into 16.7 g increments and placed into clean bottles as previously described. The bottle was then filled to the 1 L mark with filtered water. All solutions were then placed in a warm, sonication bath for 30 minutes to allow all components of the broths to evenly solubilize. Broths were placed in the refrigerator until they were administered to the animals via water bottle administration for 2 weeks prior to TMD induction.

Adult Sprague-Dawley male rats (200 g-300 g) were housed separately in clean, standard plastic rat cages (VWR, West Chester, Pa.) with non-restricted access to both food and water in a room with 12 hour/light dark cycles. Three consecutive days prior to testing, animals were allowed to enter the Ugo Basile Durham animal holding device (Ugo Basile, Collegeville, Pa.) for 5 min to acclimate to testing conditions. During this acclimation period, stimulation of hair follicles and epidermis located in the masseter and TMJ region of the face occurred by gently rubbing the area with a pipette tip. This stimulation was used to improve the condition of the animal to the testing procedure, thus reducing the number of false reactions to testing filaments. Baseline nocifensive behaviors were assessed by utilizing a modified version of the well-established von Frey method. A series of calibrated von Frey filaments were applied in increasing force to the cutaneous area over the masseter muscle. Prior to application, the muscle was palpated with the tip of the testing filament to insure proper placement. Once placement was established, a scientist blinded to the experimental conditions placed enough force on the location to accomplish a bend in the filament. Reactions observed after initiation of force to the area and prior to the bend of the filament, were verified by one other scientist and recorded. Each filament was applied 5 times, and recorded as the number of reactions obtained from 5 applications of each specific calibrated filament. Measurements were collected over both the right and left masseter muscles of each animal, which were averaged together to obtain a combined average number of reactions out of 5. Baseline readings were prior to 2 week feeding of all chicken broth products and again 24 hours prior to TMD induction.

Figure 3:
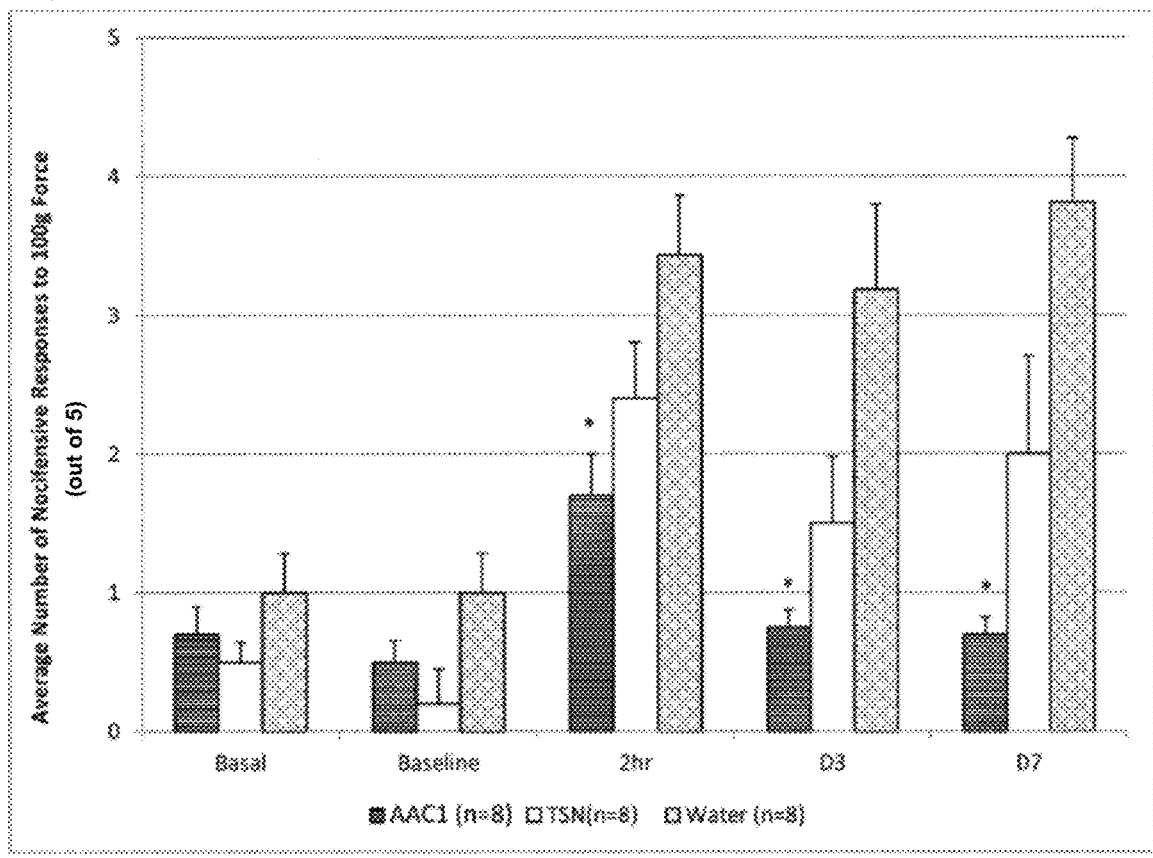
FIG. 3 shows nocifensive responses of AAC1 compared to a commercial product.

The number of nocifensive responses after 2 hr, 3 days, or 7 days in animals experiencing a mechanically induced TMD pathology was measured. The results of this study, which are shown in FIG. 3, demonstrate that AAC1 significantly reduces the number of nocifensive responses after 2 hr, 3 days, or 7 days in animals experiencing a mechanically induced TMD pathology. AAC1 significantly decreases the number of nocifensive responses as compared to TMD animals that consumed only water. The TSN product did not cause a decrease in nocifensive responses at any of the measured time points. Thus, while product AAC1 reduces nocifensive behaviors in animals experiencing chronic inflammation resulting from the prolonged jaw opening TMD model, this ability is not exhibited by a commercially available product. Based on results obtained from previous examples, as well as data presented in this example, we would predict that a homemade broth product would not significantly reduce TMJ stress induced nocifensive responses.

Example 9 Effect of Broth on Various Diseases Through Epigenetic Changes

The goal of this study was to evaluate the effects of daily administration of chicken broth on miRNAs implicated in the development and resolution of neurological inflammatory conditions and diseases. miRNAs are small RNA molecules (typically about 22-nucleotide long) that play an important role in regulating the genome of animals including humans. These molecules control the genetic expression of thousands of genes. Importantly, changes in the expression of miRNAs are implicated in the development and progression of many inflammatory and disease states.

Adult Sprague-Dawley male rats (200 g-300 g) were housed separately in clean, standard plastic rat cages (VWR, West Chester, Pa.) with non-restricted access to both food and water in a room with 12 hour/light dark cycles. Chicken broth AAC1 (8% solids) and a homemade-style broth (1.7% solids) were used in this test. Broth AAC1 was made at a 1% (w/v) by placing 10 g (1%) of powdered broth in a clean, autoclaved bottle. The bottle was then filled to the 1 L mark with filtered water. To maintain comparison ratios of percent solids between AAC1 and a homemade-style broth, the homemade broth was diluted 8 fold with filtered water by placing 125 mL of stock broth, and diluting the broth to 1 L. Solutions were then placed in a warm, sonication bath for 30 minutes to allow all components of the broths to evenly go into solution. Broths were placed in the refrigerator until they were to be used. Animals received 300 mL of broth every two days for a total of 4 weeks. Spinal trigeminal nucleus (STN) and frontal cortex (FC) samples were acquired from the animals, while pancreatic tissue samples were obtained via abdominal dissection. Once extracted, tissues were immediately frozen in liquid nitrogen, and stored at $-20°$ C. until RNA could be extracted.

Tissues were weighed, and placed into a 1.5 mL Eppendorf tube (Eppendorf, Hauppauge, N.Y.) containing 600 µl TRIzol® Reagent (Invitrogen, Grand Island, N.Y.). Tissues were homogenized using a plastic pestle in a clean, RNAase free hood. Once tissues were completely homogenized, 600 µl of TRIzol added to each sample, and inverted several times to ensure complete mixing. Once mixed, 120 µl chloroform was placed in each tube, and rapidly inverted. Samples were then placed on ice for 5 minutes. After 5 minutes, samples were centrifuged at 12,000×g for 15 minutes at 4° C. to separate the organic and aqueous layers. Once separated, the RNA containing aqueous layer was removed and placed into a clean, 1.5 mL tube. At this time, an additional 120 µl chloroform was placed in each tube, and rapidly inverted. Samples were again incubated on ice for 5 minutes and centrifuged at 12,000×g for 15 minutes at 4° C. Once separated, the RNA containing aqueous layer was removed and placed into a clean, 1.5 mL tube. To precipitate the RNA, 1 mL of ice cold isopropanol was placed in each tube. Each sample was then inverted several times to insure complete mixing. Samples were then incubated at $-20°$ C. for 30 minutes and centrifuged at 12,000×g for 15 minutes at 4° C. RNA pellets were first visualized, and isopropanol was removed. RNA pellets were then washed with RNAase free 75% ethanol, and centrifuged 7,500×g for 10 minutes at 4° C. Ethanol was then removed and the RNA pellets allowed to dry. Pellets were then re-suspended in RNAase free water, and placed at $-20°$ C.

cDNA was obtained from total RNA samples (250 ng) using the miScript 2 RT Kit (Qiagen) according to manufacturer's manual. Samples were incubated at 37° C. for 1 hour, followed by incubation at 95° C. for 5 minutes. This cycle was completed once, at which time the sample was placed on ice. Samples not assayed immediately were placed at $-20°$ C. for storage, while samples to be assayed immediately were diluted with 200 µl of RNAase free water as described in manufacture's handbook.

Qiagen Pathway-Focused RT-PCR arrays were used to determine changes in miRNA expression using panels focused on Diabetic, Inflammatory & Autoimmune, and Neurological Development & Diseases pathways. QuantiText SYBR Green PCR Master Mix (2×), miScript Universal Primer (10×), template cDNA, and RNAase free water was allowed to come to room temperature prior to use. In a clean, RNAase-free environment the following components were combined in the following amounts to a clean, RNAase-free reservoir as described in manufacturer's handbook. Once mixed, 25 µl of prepared reaction was pipetted into each well of a 96 well Pathway Focused RT-PCR plate using a multichannel pipette. Once loaded, samples were covered with a provided, clear, plastic adhesive sheet, and each well sealed individually. Each plate was placed in an Applied Biosystems OneStep RT-PCR machine where it was incubated initially at 95° C. for 15 minutes, then 40 cycles at the following conditions: 94° C. 15 seconds; 55° C. for 30 seconds; and 70° C. for 30 seconds. Data collection occurred during the second step of each cycle of 40.

Once each experiment was completed, raw data was imported into OneStep software. Prior to analysis, a baseline was established according to manufacturer's specification listed in the protocol handbook (cycle 2-2 cycles prior to amplification, not more than cycle 15). The baseline is the noise level in early cycle, where there is no detectable amplification. At this point a threshold was also established according to manufacturer's specifications detailed in the handbook. Thresholds were set using a logarithmic amplification plot to include the log-linear range of the curve. The threshold was placed at 1 for all arrays. This position allowed the threshold to be set above background noise, and at the lower half of the linear portion of the curve for all control samples. Under these conditions, raw CT values were obtained.

To obtain ΔCT values, raw CT values from one control sample (n=3) and one chicken broth sample (n=3) for each panel was placed in miScrip miRNA PCR Array Web-Based software provided by the manufacture. Data was normalized to a minimum of 2 housekeeping genes, since typically levels of these genes do not change under experimental conditions. Once appropriate housekeeping genes were selected, data was submitted, and normalized ΔCT values were calculated by web-based software. Values obtained from data software were then placed into an excel spreadsheet. To calculate ΔΔCT values for chicken broth samples the following equation was used: $\Delta\Delta CT_{AAC1} = \Delta CT_{control\ sample1} - \Delta CT_{AAC1\ sample1}$. To determine fold change from control expression the following equation was used: fold change=$2^{\wedge}\Delta\Delta CT_{AAC1\ sample1}$. Fold changes obtained from 3 independent experiments were averaged, and reported as the average fold change±SDEV. Statistical significance was determined through Mann-Whitney U, and significance determined when $p \leq 0.05$.

TABLE 7

Changes in miRNA levels associated with inflammation and autoimmune diseases in response to AAC1

| Name | Pathology | Targets If Known | Average Fold Change Control AAC1 | P Values Vs. Control | Sequence |
|---|---|---|---|---|---|
| rno-miR-101a-3p | Inflammation and Autoimmune | Fos, Ptgs2, Rac1, Socs2, Spred1 | 1.00 ± 0.07<br>0.69 ± 0.07 | 0.05 | UACAGUACUGUGAUAACUGAA<br>SEQ ID No. 1 |
| rno-miR-101b-3p | Inflammation and Autoimmune | Fos, Ptgs2, Rac1, Socs2, Spred1 | 1.00 ± 0.06<br>0.68 ± 0.05 | 0.046 | UACAGUACUGUGAUAGCUGAA<br>SEQ ID No. 2 |

TABLE 7-continued

Changes in miRNA levels associated with inflammation and autoimmune diseases in response to AAC1

| Name | Pathology | Targets If Known | Average Fold Change Control AAC1 | P Values Vs. Control | Sequence |
|---|---|---|---|---|---|
| rno-miR-106b-5p | Inflammation and Autoimmune | F3, Il25, Mgll, Osm. | 1.00 ± 0.06<br>0.65 ± 0.08 | 0.046 | UAAAGUGCUGACAGUGCAGAU<br>SEQ ID No. 3 |
| rno-miR-125b-5p | Inflammation and Autoimmune | Il16, Irf4, Stat3, Tnfsf4. | 1.00 ± 0.05<br>0.78 ± 0.09 | 0.046 | UCCCUGAGACCCUAACUUGUGA<br>SEQ ID No. 4 |
| rno-miR-140-5p | Inflammation and Autoimmune | Bmp2, Fgf9, Hdac7, Spred1, Vegfa. | 1.00 ± 0.09<br>0.78 ± 0.06 | 0.05 | CAGUGGUUUUACCCUAUGGUAG<br>SEQ ID No. 5 |
| rno-miR-142-3p | Inflammation and Autoimmune | Ghr, Prlr, Rac1. | 1.00 ± 0.05<br>0.69 ± 0.04 | 0.05 | UGUAGUGUUUCCUACUUUAUGGA<br>SEQ ID No. 6 |
| rno-miR-16-5p | Inflammation and Autoimmune | Btla, Cd28, Fgf7, Ghr, Il10ra, Spred1, Vegfa. | 1.00 ± 0.05<br>0.68 ± 0.10 | 0.046 | UAGCAGCACGUAAAUAUUGGCG<br>SEQ ID No. 7 |
| rno-miR-17-5p | Inflammation and Autoimmune | F3, Il25, Mgll, Osm. | 1.00 ± 0.10<br>0.54 ± 0.08 | 0.05 | CAAAGUGCUUACAGUGCAGGUAG<br>SEQ ID No. 8 |
| rno-miR-195-5p | Inflammation and Autoimmune | Btla, Cd28, Fgf7, Ghr, Il10ra, Spred1, Vegfa | 1.00 ± 0.06<br>0.65 ± 0.12 | 0.05 | UAGCAGCACAGAAAUAUUGGC<br>SEQ ID No. 9 |
| rno-miR-19a-3p | Inflammation and Autoimmune | Bmp3, Cast, Cntfr, F3 | 1.00 ± 0.13<br>0.45 ± 0.06 | 0.05 | UGUGCAAAUCUAUGCAAAACUGA<br>SEQ ID No. 10 |
| rno-miR-19b-3p | Inflammation and Autoimmune | Bmp3, Cast, Cntfr, F3 | 1.00 ± 0.09<br>0.42 ± 0.04 | 0.05 | UGUGCAAAUCCAUGCAAAACUGA<br>SEQ ID No. 11 |
| rno-miR-20a-5p | Inflammation and Autoimmune | F3, Il25, Mgll, Osm. | 1.00 ± 0.09<br>0.62 ± 0.01 | 0.046 | UAAAGUGCUUAUAGUGCAGGUAG<br>SEQ ID No. 12 |
| rno-miR-20b-5p | Inflammation and Autoimmune | F3, Il25, Mgll, Osm. | 1.00 ± 0.06<br>0.62 ± 0.05 | 0.05 | CAAAGUGCUCAUAGUGCAGGUAG<br>SEQ ID No. 13 |
| rno-miR-23a-3p | Inflammation and Autoimmune | Ccl7, Cxcl12, Fas, Grem1, Il11, Il3, Il6ra, Kitlg, Mstn, Prkca, Prok2, Stat5b. | 1.00 ± 0.15<br>0.77 ± 0.12 | 0.05 | AUCACAUUGCCAGGGAUUUCC<br>SEQ ID No. 14 |
| rno-miR-23b-3p | Inflammation and Autoimmune | Ccl7, Cxcl12, Fas, Grem1, Il11, Il3, Il6ra, Kitlg, Mstn, Prkca, Prok2, Stat5b. | 1.00 ± 0.14<br>0.74 ± 0.12 | 0.05 | AUCACAUUGCCAGGGAUUACC<br>SEQ ID No. 15 |
| rno-miR-27a-3p | Inflammation and Autoimmune | Bmp3, Cd28, Csf1, Fgf1, Grem1, Irf4, Lifr, Mstn. | 1.00 ± 0.10<br>0.64 ± 0.04 | 0.05 | UUCACAGUGGCUAAGUUCCGC<br>SEQ ID No. 16 |

TABLE 7-continued

Changes in miRNA levels associated with inflammation and autoimmune diseases in response to AAC1

| Name | Pathology | Targets If Known | Average Fold Change Control AAC1 | P Values Vs. Control | Sequence |
|---|---|---|---|---|---|
| rno-miR-291a-3p | Inflammation and Autoimmune | Bcl6, Cyp26b1, Dock2, F3, Lefty1, Lefty2. | 1.00 ± 0.44<br>8.13 ± 3.67 | 0.05 | AAAGUGCUUCCACUUUGUGUGCC<br>SEQ ID No. 17 |
| rno-miR-29c-3p | Inflammation and Autoimmune | Hdac4, Il1rap, Lif, Pdgfa, Pdgfc, Tnfrsf1a, Vegfa | 1.00 ± 0.04<br>0.88 ± 0.02 | 0.05 | UAGCACCAUUUGAAAUCGGUUA<br>SEQ ID No. 18 |
| rno-miR-30b-5p | Inflammation and Autoimmune | Hdac5, Il1a, Irf4, Lifr | 1.00 ± 0.11<br>0.64 ± 0.16 | 0.05 | UGUAAACAUCCUACACUCAGCU<br>SEQ ID No. 19 |
| rno-miR-30d-5p | Inflammation and Autoimmune | Hdac5, Il1a, Irf4, Lifr | 1.00 ± 0.10<br>0.68 ± 0.16 | 0.05 | UGUAAACAUCCCCGACUGGAAG<br>SEQ ID No. 20 |
| rno-miR-30e-5p | Inflammation and Autoimmune | Hdac5, Il1a, Irf4, Lifr | 1.00 ± 0.14<br>0.64 ± 0.06 | 0.05 | UGUAAACAUCCUUGACUGGAAG<br>SEQ ID No. 21 |
| rno-miR-322-5p | Inflammation and Autoimmune | Btla, Cd28, Fgf7, Ghr, Il10ra, Spred1, Vegfa | 1.00 ± 0.14<br>0.63 ± 0.14 | 0.05 | CAGCAGCAAUUCAUGUUUUGGA<br>SEQ ID No. 22 |
| rno-miR-34c-5p | Inflammation and Autoimmune | Areg, Bmp3, Il6ra, Kitlg, Nampt, Nfe2l1, Serpinf2 | 1.00 ± 0.56<br>0.54 ± 0.14 | 0.05 | AGGCAGUGUAGUUAGCUGAUUGC<br>SEQ ID No. 23 |
| rno-miR-410-3p | Inflammation and Autoimmune | Csf2, F3, Fgf7, Il4, Nr3c1, Vegfa | 1.00 ± 0.10<br>0.67 ± 0.05 | 0.05 | AAUAUAACACAGAUGGCCUGU<br>SEQ ID No. 24 |
| rno-miR-449a-5p | Inflammation and Autoimmune | Areg, Bmp3, Il6ra, Kitlg, Nampt, Nfe2l1, Serpinf2 | 1.00 ± 0.06<br>0.90 ± 0.01 | 0.046 | UGGCAGUGUAUUGUUAGCUGGU<br>SEQ ID No. 25 |
| rno-miR-93-5p | Inflammation and Autoimmune | F3, Il25, Mgll, Osm | 1.00 ± 0.01<br>0.66 ± 0.04 | 0.05 | CAAAGUGCUGUUCGUGCAGGUAG<br>SEQ ID No. 26 |

TABLE 8

Changes in miRNA levels associated with diabetes in response to AAC1

| Name | Target Tissue | Average Fold Change Control AAC1 | P Values Vs. control | Sequence |
|---|---|---|---|---|
| rno-miR-184 | Adipose, beta cells, modulates insulin signaling, Down in T2DM | 1.00 ± 0.02<br>3.59 ± 2.86 | 0.05 | UGGACGGAGAACUGAUAAGGGU<br>SEQ ID No. 27 |

TABLE 8-continued

Changes in miRNA levels associated with diabetes in response to AAC1

| Name | Target Tissue | Average Fold Change Control AAC1 | P Values Vs. control | Sequence |
|---|---|---|---|---|
| rno-miR-26b-5p | Adipose, Up in T1DM | 1.00 ± 0.18<br>0.53 ± 0.10 | 0.05 | UUCAAGUAAUUCAGGAUAGGU<br>SEQ ID No. 28 |
| rno-miR-29b-3p | Adipose, Increased then impaired glucose-insulin secreation | 1.00 ± 0.33<br>0.30 ± 0.12 | 0.05 | UAGCACCAUUUGAAAUCAGUGUU<br>SEQ ID No. 29 |
| rno-miR-29c-3p | Adipose, Above | 1.00 ± 0.55<br>0.46 ± 0.15 | 0.05 | UAGCACCAUUUGAAAUCGGUUA<br>SEQ ID No. 30 |
| rno-miR-30a-5p | Adipose, initiates glucotoxisity beta cell dysfunction | 1.00 ± 0.07<br>0.82 ± 0.10 | 0.05 | UGUAAACAUCCUCGACUGGAAG<br>SEQ ID No. 31 |
| rno-miR-34a-5p | Adipose, beta cells | 1.00 ± 0.13<br>0.42 ± 0.06 | 0.05 | UGGCAGUGUCUUAGCUGGUUGU<br>SEQ ID No. 32 |
| rno-miR-370-3p | Adipose | 1.00 ± 0.21<br>0.32 ± 0.10 | 0.05 | GCCUGCUGGGGUGGAACCUGGU<br>SEQ ID No. 33 |

TABLE 9

Changes in miRNA levels associated with AAC lneurological development and in response to AAC1

| Name | Pathology | Average Fold Change Control AAC1 | P Values Vs. control | Sequence |
|---|---|---|---|---|
| rno-miR-106b-5p | Autistic Disorders, Schizophrenia, Alzheimer's | 1.00 ± 0.10<br>0.77 ± 0.13 | 0.05 | UAAAGUGCUGACAGUGCAGAU<br>SEQ ID No. 34 |
| rno-miR-138-5p | Development, Schizophrenia | 1.00 ± 0.18<br>0.69 ± 0.20 | 0.05 | AGCUGGUGUUGUGAAUCAGGCCG<br>SEQ ID No. 35 |
| rno-miR-148b-3p | Autistic Disorders | 1.00 ± 0.08<br>0.74 ± 0.11 | 0.05 | UCAGUGCAUCACAGAACUUUGU<br>SEQ ID No. 36 |
| rno-miR-195-5p | Schizophrenia | 1.00 ± 0.05<br>0.87 ± 0.04 | 0.046 | UAGCAGCACAGAAAUAUUGGC<br>SEQ ID No. 37 |
| rno-miR-19b-3p | Alzheimer's, Spinocerebellar Ataxia | 1.00 ± 0.17<br>0.65 ± 0.18 | 0.05 | UGUGCAAAUCCAUGCAAAACUGA<br>SEQ ID No. 38 |
| rno-miR-20b-5p | Schizophrenia | 1.00 ± 0.14<br>0.78 ± 0.12 | 0.05 | CAAAGUGCUCAUAGUGCAGGUAG<br>SEQ ID No. 39 |
| rno-miR-26b-5p | Schizophrenia, Alzheimer's | 1.00 ± 0.06<br>0.76 ± 0.08 | 0.05 | UUCAAGUAAUUCAGGAUAGGU<br>SEQ ID No. 40 |
| rno-miR-342-3p | Prion Disease | 1.00 ± 0.06<br>0.81 ± 0.08 | 0.05 | UCUCACACAGAAAUCGCACCCGU<br>SEQ ID No. 41 |
| rno-miR-409a-3p | Schizophrenia | 1.00 ± 0.08<br>0.72 ± 0.07 | 0.05 | AUGUUGCUCGGUGAACCCC<br>SEQ ID No. 42 |
| rno-miR-598-3p | Autistic Disorders | 1.00 ± 0.12<br>0.77 ± 0.07 | 0.05 | UACGUCAUCGUCGUCAUCGUUA<br>SEQ ID No. 43 |

Spinal cord samples obtained from animals fed 1% chicken broth AAC1 for 28 days showed significant repression of 26 miRNAs implicated in inflammation as compared to the levels found in animals treated with the control samples. Interestingly, miRNA of the 101 family (See Table 7), which has been shown to inhibit Map Kinase Phosphatase 1, were among those that are inhibited by AAC1 broth. Frontal cortex samples obtained from animals fed 1% AAC1 chicken broth also showed a significant reduction in the expression of 10 miRNAs implicated in the development of multiple neurological diseases. These diseases include Autism, Schizophrenia, Alzheimer's, Spinocerebellar Ataxia, and Prion's diseases.

Taken together, the results from this study suggest that the chicken broth AAC1 may be beneficial in the epigenetic prophylactic regulation of certain miRNAs implicated in neurological inflammation of the central nervous system, the development and progression of certain neurological diseases, as well as in the pathogenesis of metabolic syndrome. These data suggest that chicken broth AAC1 is more effective in regulating these miRNAs than a homemade product prepared from the same raw materials.

Example 10 Protein Profiles and Quantification of Protein Molecular Weight Distribution The goal of this study was to differentiate protein profiles in different chicken broth samples through gel electrophoresis. Gel electrophoresis was performed on all the samples to separate protein content by molecular weight. Protein content was visualized using a Simple Blue Safe Stain. Approximate molecular weights of any discernable protein bands were determined.

Figure 4:
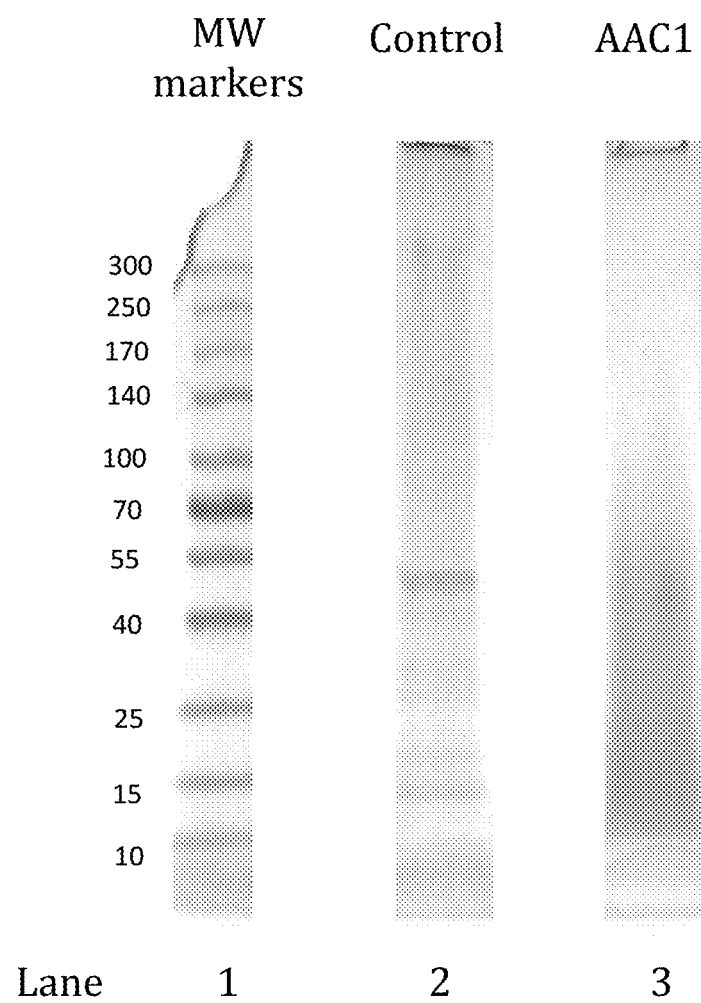
FIG. 4 shows the protein profile by staining of proteins separated by SDS-PAGE and quantification of molecular weight distribution.

Two samples, a control sample containing most major proteins from chickens (lane 2) and AAC1 broth (lane 3) were Diluted in DI water to a final concentration of 1% Solid and analyzed by SDS-PAGE (FIG. 4) along with a molecular weight (MW) marker (lane 1). The distribution of major protein bands were quantitated. Different banding patterns may be a result of different processing methods. As shown in FIG. 4, AAC1 had a smearing pattern indicating high levels of protein degradation which may be attributed to the production process used to make this product. At least 90% of the proteins in AAC1 were within the range of 10-50 kD. This is in contrast with the control sample, which showed a much broader distribution of MW from 10 kD to 300 kD.

All animal studies described herein were performed using approved protocols in compliance with government rules and regulations. Changes may be made in the above methods and systems without departing from the scope hereof. It should thus be noted that the matter contained in the above description or shown in the accompanying drawings should be interpreted as illustrative and not in a limiting sense. The following claims are intended to cover generic and specific features described herein, as well as statements of the scope of the present method and system, which, as a matter of language, might be said to fall there between.

Although each of the embodiments described above has been illustrated with various components having particular respective orientations, it should be understood that the system and methods as described in the present disclosure may take on a variety of specific configurations with the various components being located in a variety of positions and mutual orientations and still remain within the spirit and scope of the present disclosure. Furthermore, suitable equivalents may be used in place of or in addition to the various components, the function and use of such substitute or additional components being held to be familiar to those skilled in the art and are therefore regarded as falling within the scope of the present disclosure. Therefore, the present examples are to be considered as illustrative and not restrictive, and the present disclosure is not to be limited to the details given herein but may be modified within the scope of the appended claims.

All references cited in this disclosure, including patents, patent applications, scientific papers and other publications, are hereby incorporated by reference into this application.

We claim:

1. A method of treating a joint disease, comprising administering to a subject an effective amount of a composition prepared from poultry parts, said composition comprising an enhanced quantity of chondroitin sulfate and having certain ratio between amino acids proline and histidine derived from said poultry parts, wherein the amount of chondroitin sulfate derived from said poultry parts is at least 6% by weight of total dry solids of the composition, and wherein said certain ratio between proline and histidine derived from said poultry parts is at least 4:1 by weight, said composition being in solid or liquid form, wherein at least 50% of proteins in said composition have a molecular weight of between 15 kD and 70 kD.

2. The method of claim 1, wherein said composition reduces expression level of protein kinase A (PKA) by at least 50% in a subject administered said composition as compared to a control subject not administered said composition.

3. The method of claim 1, wherein said composition inhibits COX-2 activity by at least 20% in said subject while not significantly inhibiting COX1 activity.

4. The method of claim 3, wherein the ratio of inhibition between COX2 and COX1 exerted by the composition is between 2 and 30.

5. The method of claim 1, wherein said composition significantly reduces nociception (pain) as compared to a control subject not administered said composition.

6. The method of claim 1, wherein said composition decreases expression of at least one miRNA in said subject receiving said composition as compared to expression of said miRNA in a control subject not receiving said composition, wherein said at least one miRNA is a member selected from the group consisting of SEQ ID Nos. 1-16, and 18-26.

7. The method of claim 1, wherein said composition decreases expression of at least one miRNA in said subject receiving said composition as compared to expression of said miRNA in a control subject not receiving said composition, wherein said at least one miRNA is a member selected from the group consisting of SEQ ID Nos. 28-33.

8. The method of claim 1, wherein said composition decreases expression of at least one miRNA in said subject receiving said composition as compared to expression of said miRNA in a control subject not receiving said composition, wherein said at least one miRNA is a member selected from the group consisting of SEQ ID Nos. 34-43.

9. The method of claim 1, wherein said composition is in a liquid form and wherein said composition further comprises a polyphenol compound derived from said poultry parts at a concentration of at least 4,000 μg/ml GAE (Gallic Acid Equivalent).

10. The method of claim 1, wherein the ratio between proline and histidine derived from said poultry parts is at least 6:1 by weight.

11. The method of claim 1, wherein said proline derived from said poultry parts is present in said composition by at least 8% (w/w) on solid basis.

12. The method of claim 1, wherein said composition further comprises hydroxyproline derived from said poultry parts, wherein the ratio between the hydroxyproline and histidine derived from said poultry parts in said composition is at least 4:1 by weight, and wherein said hydroxyproline derived from said poultry parts is present in said composition by at least 7% (w/w) on solid basis.

13. The method of claim 1, wherein said composition further comprises one or more branched chain amino acids (BCAA) derived from said poultry parts, said BCAA being at least one member selected from the group consisting of leucine, isoleucine, and valine, wherein the amount of said BCAA derived from said poultry parts is at least 5% by weight of total amino acids in said composition.

* * * * *

```
                          SEQUENCE LISTING

<160> NUMBER OF SEQ ID NOS: 43

<210> SEQ ID NO 1
<211> LENGTH: 21
<212> TYPE: RNA
<213> ORGANISM: Rattus norvegicus

<400> SEQUENCE: 1
uacaguacug ugauaacuga a                                               21

<210> SEQ ID NO 2
<211> LENGTH: 21
<212> TYPE: RNA
<213> ORGANISM: Rattus norvegicus

<400> SEQUENCE: 2
uacaguacug ugauagcuga a                                               21

<210> SEQ ID NO 3
<211> LENGTH: 21
<212> TYPE: RNA
<213> ORGANISM: Rattus norvegicus

<400> SEQUENCE: 3
```

-continued uaaagugcug acagugcaga u                    21

<210> SEQ ID NO 4
<211> LENGTH: 22
<212> TYPE: RNA
<213> ORGANISM: Rattus norvegicus

<400> SEQUENCE: 4
ucccugagac ccuaacuugu ga                    22

<210> SEQ ID NO 5
<211> LENGTH: 22
<212> TYPE: RNA
<213> ORGANISM: Rattus norvegicus

<400> SEQUENCE: 5
cagugguuuu acccuauggu ag                    22

<210> SEQ ID NO 6
<211> LENGTH: 23
<212> TYPE: RNA
<213> ORGANISM: Rattus norvegicus

<400> SEQUENCE: 6
uguaguguuu ccuacuuuau gga                   23

<210> SEQ ID NO 7
<211> LENGTH: 22
<212> TYPE: RNA
<213> ORGANISM: Rattus norvegicus

<400> SEQUENCE: 7
uagcagcacg uaaauauugg cg                    22

<210> SEQ ID NO 8
<211> LENGTH: 23
<212> TYPE: RNA
<213> ORGANISM: Rattus norvegicus

<400> SEQUENCE: 8
caaagugcuu acagugcagg uag                   23

<210> SEQ ID NO 9
<211> LENGTH: 21
<212> TYPE: RNA
<213> ORGANISM: Rattus norvegicus

<400> SEQUENCE: 9
uagcagcaca gaaauauugg c                     21

<210> SEQ ID NO 10
<211> LENGTH: 23
<212> TYPE: RNA
<213> ORGANISM: Rattus norvegicus

<400> SEQUENCE: 10
ugugcaaauc uaugcaaaac uga                   23

<210> SEQ ID NO 11
<211> LENGTH: 23
<212> TYPE: RNA
<213> ORGANISM: Rattus norvegicus

```
<400> SEQUENCE: 11
ugugcaaauc caugcaaaac uga                                          23

<210> SEQ ID NO 12
<211> LENGTH: 23
<212> TYPE: RNA
<213> ORGANISM: Rattus norvegicus

<400> SEQUENCE: 12
uaaagugcuu auagugcagg uag                                          23

<210> SEQ ID NO 13
<211> LENGTH: 23
<212> TYPE: RNA
<213> ORGANISM: Rattus norvegicus

<400> SEQUENCE: 13
caaagugcuc auagugcagg uag                                          23

<210> SEQ ID NO 14
<211> LENGTH: 21
<212> TYPE: RNA
<213> ORGANISM: Rattus norvegicus

<400> SEQUENCE: 14
aucacauugc cagggauuuc c                                            21

<210> SEQ ID NO 15
<211> LENGTH: 21
<212> TYPE: RNA
<213> ORGANISM: Rattus norvegicus

<400> SEQUENCE: 15
aucacauugc cagggauuac c                                            21

<210> SEQ ID NO 16
<211> LENGTH: 21
<212> TYPE: RNA
<213> ORGANISM: Rattus norvegicus

<400> SEQUENCE: 16
uucacagugg cuaaguuccg c                                            21

<210> SEQ ID NO 17
<211> LENGTH: 23
<212> TYPE: RNA
<213> ORGANISM: Rattus norvegicus

<400> SEQUENCE: 17
aaagugcuuc cacuuugugu gcc                                          23

<210> SEQ ID NO 18
<211> LENGTH: 22
<212> TYPE: RNA
<213> ORGANISM: Rattus norvegicus

<400> SEQUENCE: 18
uagcaccauu ugaaaucggu ua                                           22

<210> SEQ ID NO 19
<211> LENGTH: 22
<212> TYPE: RNA
<213> ORGANISM: Rattus norvegicus
```

```
<400> SEQUENCE: 19
uguaaacauc cuacacucag cu                                          22

<210> SEQ ID NO 20
<211> LENGTH: 22
<212> TYPE: RNA
<213> ORGANISM: Rattus norvegicus

<400> SEQUENCE: 20
uguaaacauc cccgacugga ag                                          22

<210> SEQ ID NO 21
<211> LENGTH: 22
<212> TYPE: RNA
<213> ORGANISM: Rattus norvegicus

<400> SEQUENCE: 21
uguaaacauc cuugacugga ag                                          22

<210> SEQ ID NO 22
<211> LENGTH: 22
<212> TYPE: RNA
<213> ORGANISM: Rattus norvegicus

<400> SEQUENCE: 22
cagcagcaau ucauguuuug ga                                          22

<210> SEQ ID NO 23
<211> LENGTH: 23
<212> TYPE: RNA
<213> ORGANISM: Rattus norvegicus

<400> SEQUENCE: 23
aggcagugua guuagcugau ugc                                         23

<210> SEQ ID NO 24
<211> LENGTH: 21
<212> TYPE: RNA
<213> ORGANISM: Rattus norvegicus

<400> SEQUENCE: 24
aauauaacac agauggccug u                                           21

<210> SEQ ID NO 25
<211> LENGTH: 22
<212> TYPE: RNA
<213> ORGANISM: Rattus norvegicus

<400> SEQUENCE: 25
uggcagugua uuguuagcug gu                                          22

<210> SEQ ID NO 26
<211> LENGTH: 23
<212> TYPE: RNA
<213> ORGANISM: Rattus norvegicus

<400> SEQUENCE: 26
caaagugcug uucgugcagg uag                                         23

<210> SEQ ID NO 27
<211> LENGTH: 22
<212> TYPE: RNA
```

```
<213> ORGANISM: Rattus norvegicus

<400> SEQUENCE: 27
uggacggaga acugauaagg gu                                              22

<210> SEQ ID NO 28
<211> LENGTH: 21
<212> TYPE: RNA
<213> ORGANISM: Rattus norvegicus

<400> SEQUENCE: 28
uucaaguaau ucaggauagg u                                               21

<210> SEQ ID NO 29
<211> LENGTH: 23
<212> TYPE: RNA
<213> ORGANISM: Rattus norvegicus

<400> SEQUENCE: 29
uagcaccauu ugaaaucagu guu                                             23

<210> SEQ ID NO 30
<211> LENGTH: 22
<212> TYPE: RNA
<213> ORGANISM: Rattus norvegicus

<400> SEQUENCE: 30
uagcaccauu ugaaaucggu ua                                              22

<210> SEQ ID NO 31
<211> LENGTH: 22
<212> TYPE: RNA
<213> ORGANISM: Rattus norvegicus

<400> SEQUENCE: 31
uguaaacauc cucgacugga ag                                              22

<210> SEQ ID NO 32
<211> LENGTH: 22
<212> TYPE: RNA
<213> ORGANISM: Rattus norvegicus

<400> SEQUENCE: 32
uggcaguguc uuagcugguu gu                                              22

<210> SEQ ID NO 33
<211> LENGTH: 22
<212> TYPE: RNA
<213> ORGANISM: Rattus norvegicus

<400> SEQUENCE: 33
gccugcuggg guggaaccug gu                                              22

<210> SEQ ID NO 34
<211> LENGTH: 21
<212> TYPE: RNA
<213> ORGANISM: Rattus norvegicus

<400> SEQUENCE: 34
uaaagugcug acagugcaga u                                               21

<210> SEQ ID NO 35
<211> LENGTH: 23
```

<210> SEQ ID NO 35
<211> LENGTH: 23
<212> TYPE: RNA
<213> ORGANISM: Rattus norvegicus

<400> SEQUENCE: 35 agcuggguguu gugaaucagg ccg                                           23

<210> SEQ ID NO 36
<211> LENGTH: 22
<212> TYPE: RNA
<213> ORGANISM: Rattus norvegicus

<400> SEQUENCE: 36
ucagugcauc acagaacuuu gu                                             22

<210> SEQ ID NO 37
<211> LENGTH: 21
<212> TYPE: RNA
<213> ORGANISM: Rattus norvegicus

<400> SEQUENCE: 37
uagcagcaca gaaauauugg c                                              21

<210> SEQ ID NO 38
<211> LENGTH: 23
<212> TYPE: RNA
<213> ORGANISM: Rattus norvegicus

<400> SEQUENCE: 38
ugugcaaauc caugcaaaac uga                                            23

<210> SEQ ID NO 39
<211> LENGTH: 23
<212> TYPE: RNA
<213> ORGANISM: Rattus norvegicus

<400> SEQUENCE: 39
caaagugcuc auagugcagg uag                                            23

<210> SEQ ID NO 40
<211> LENGTH: 21
<212> TYPE: RNA
<213> ORGANISM: Rattus norvegicus

<400> SEQUENCE: 40
uucaaguaau ucaggauagg u                                              21

<210> SEQ ID NO 41
<211> LENGTH: 23
<212> TYPE: RNA
<213> ORGANISM: Rattus norvegicus

<400> SEQUENCE: 41
ucucacacag aaaucgcacc cgu                                            23

<210> SEQ ID NO 42
<211> LENGTH: 19
<212> TYPE: RNA
<213> ORGANISM: Rattus norvegicus

<400> SEQUENCE: 42
auguugcucg gugaaccccc                                                19

<210> SEQ ID NO 43

```
<211> LENGTH: 22
<212> TYPE: RNA
<213> ORGANISM: Rattus norvegicus

<400> SEQUENCE: 43
uacgucaucg ucgucaucgu ua                                              22
```